United States Patent [19]

Miura et al.

[11] Patent Number: 4,811,592
[45] Date of Patent: Mar. 14, 1989

[54] SPECIFIC GRAVITY DETECTOR

[75] Inventors: Shinsuke Miura; Susumu Ishizuka, both of Tokyo, Japan

[73] Assignee: Yamaichi Electric Mfg. Co., Ltd., Tokyo, Japan

[21] Appl. No.: 125,986

[22] Filed: Nov. 27, 1987

[30] Foreign Application Priority Data

Nov. 28, 1986 [JP] Japan .................. 61-285672

[51] Int. Cl.$^4$ ............................................. G01N 9/24
[52] U.S. Cl. ................................................. 73/32 A
[58] Field of Search ................................ 73/32 A, 54

[56] References Cited

U.S. PATENT DOCUMENTS 4,240,285 12/1980 Langdon .............................. 73/32 A
4,345,456 8/1982 Ponzi ................................... 73/32 A Primary Examiner—Stewart J. Levy
Assistant Examiner—Joseph W. Roskos
Attorney, Agent, or Firm—Wenderoth, Lind & Ponack

[57] ABSTRACT

A specific gravity detector includes an electromechanical vibrator having a central axis and capable of vibrating about the central axis, a transmission shaft having one end thereof connected coaxially to the vibrator, and a detector member connected coaxially to the other end of the transmission shaft. The detector member is immersed in liquid, the specific gravity of which is to be measured and vibrated about the central axis of the vibrator within the liquid by the vibration of the vibrator transmitted through the transmission shaft to measure the specific gravity of the liquid based on a variation in the resonance frequency of the vibrator corresponding to the moment of inertia of the liquid.

2 Claims, 4 Drawing Sheets

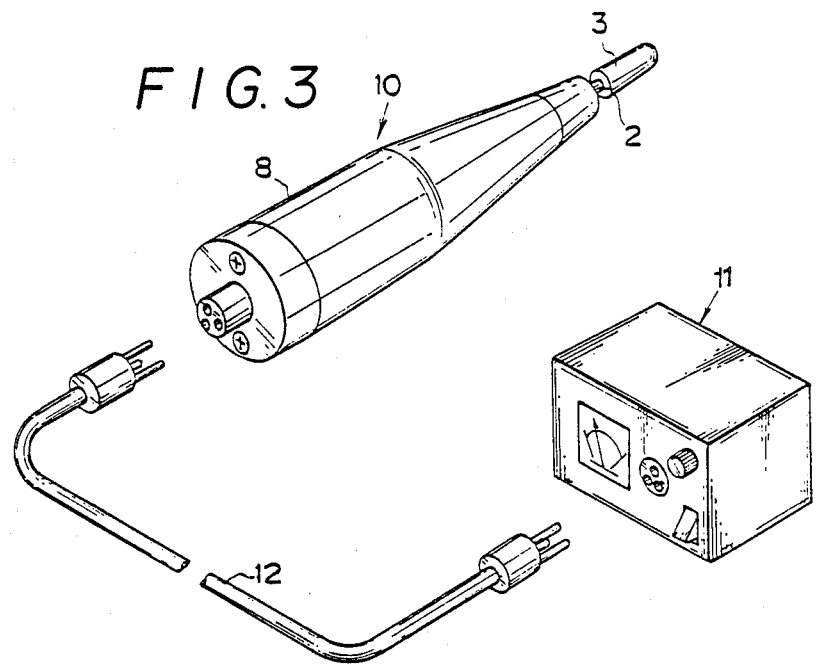
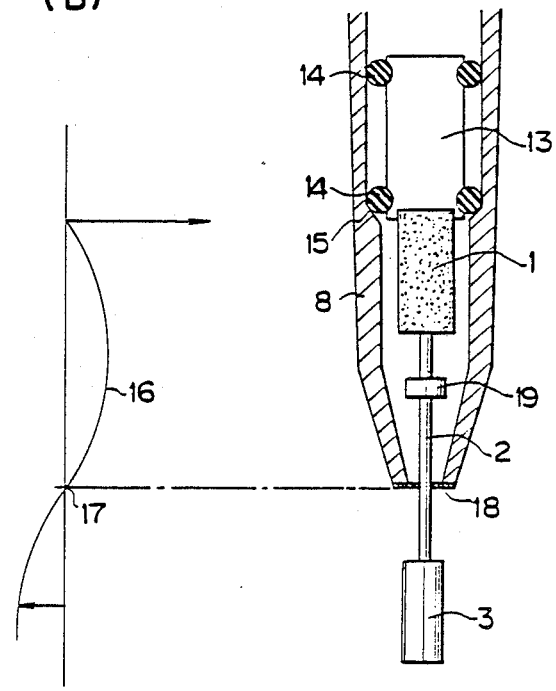

(A)

(B)

(A)

(B)

SPECIFIC GRAVITY DETECTOR

BACKGROUND OF THE INVENTION AND RELATED ART STATEMENT

The present invention relates to a specific gravity detector using an electromechanical vibrator which comprises piezoelectric ceramic members, for example, and vibrates about its central axis, and has a detector member which is immersed in liquid to measure the specific gravity thereof and which is vibrated via the electromechanical vibrator about its central axis, which central axis is coaxial with the central axis of the electromechanical vibrator, to measure the specific gravity of the liquid based on a variation in the resonance frequency of the vibrator corresponding to the moment of inertial of the liquid.

Float-type and tuning fork-type specific gravity detectors are typical ones which have heretofore been proposed in the art. The float-type specific gravity detector detects the amount of rise and fall of a float member within liquid to measure the specific gravity of the liquid. The tuning fork-type specific gravity detector detects the variation in the resonance frequency of its forks filled with liquid to be measured to measure the specific gravity of the liquid.

The float-type specific gravity detector has limited utility due to the facts that the float member has to be horizontally placed in position and a large volume of sample liquid must be prepared. It further has disadvantages in that is is mechanically complex and is likely to have to be large in size and in that high precision measurement cannot be expected.

The tuning fork-type specific gravity detector is required to have its U-shaped forks filled with sample liquid and, if the amount of the liquid in the forks is insufficient, the accuracy of the measurement is unsatisfactory. Further, since sound waves are propagated within the liquid contained in the container in which the forks are immersed, and are reflected by the inner walls of the container, an error in measurement will be made depending on the size of the container.

The present inventors conducted studies on a specific gravity detector capable of eliminating the aforementioned disadvantages and conceived a method of measuring the specific gravity of liquid by using an electromechanical vibrator, connecting the vibrator to a detector member, immersing the detector member within the liquid, transmitting the mechanical vibration of the vibrator to the detector member, and converting a variation in the resonance frequency of the vibrator corresponding to the moment of inertia of the liquid into equivalent electric vibration. In accordance with their idea, they tried to use a commercially available vibrator vibrating in the direction of its thickness as the electromechanical vibrator. As a result, it was found that the vibrator connected to a detector member caused the detector member to be vibrated vertically relative to the surface of the liquid, thereby producing vibration waves propagating within the liquid and thus making it difficult to measure the specific gravity of the liquid with a high degree of precision.

OBJECT AND SUMMARY OF THE INVENTION

The main object of the present invention is to be inexpensively provide a specific gravity detector having a simple construction, and that is, light and capable of effectively preventing the generation of a wave which is a disturbance factor, within liquid, the specific gravity of the liquid to be measurable over a wide range with a high degree of precision.

To attain the object described above, according to the present invention, there is provided a specific gravity detector comprising an electromechanical vibrator having a central axis and capable of vibrating about the central axis, a transmission shaft having one end thereof connected coaxially to the vibrator, and a detector member connected coaxially to the other end of the transmission shaft, the detector member being immersed in liquid, the specific gravity of which is to be measured, and vibrated about the central axis of the vibrator within the liquid by the vibration of the vibrator transmitted through the transmission shaft to measure the specific gravity of the liquid based on a variation in the resonance frequency of the vibrator corresponding to the moment of inertia of the liquid and imparted to the detector member.

The above and other objects, characteristic features and advantages of the present invention will become more apparent to those skilled in the art by the following description of the preferred embodiment of the invention, as illustrated in the accompanying drawings.

BRIEF DESCRIPTION OF THE DRAWINGS

FIG. 3 is a perspective view illustrating a detection section incorporating part of the detection structure, and a measuring device.

FIG. 4(A) is a longitudinal sectional view illustrating the detection section.

FIG. 4(B) is a diagram illustrating a waveform of a resonance wave of an electromechanical vibrator vibrating about its central axis.

DETAILED DESCRIPTION OF THE PREFERRED EMBODIMENT

Figure 1:
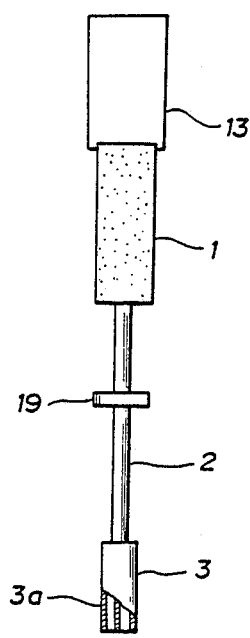
FIG. 1 is a side view illustrating the detection structure of one embodiment of the specific gravity detector according to the present invention.
Figure 5:
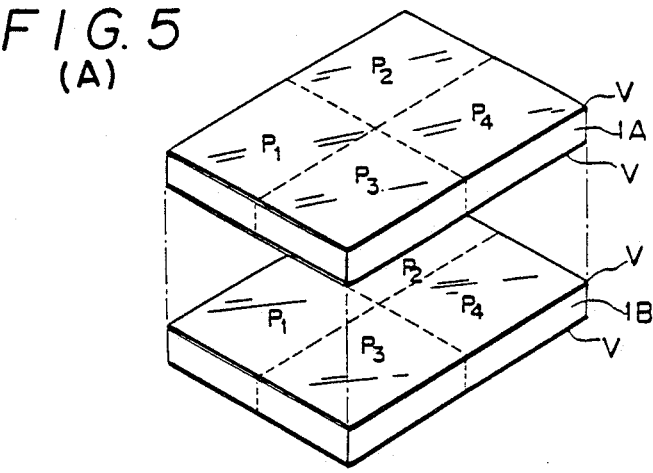
FIG. 5(A) is an exploded perspective view illustrating one example of the vibrator.
FIG. 5(B) is a side view illustrating the vibrator of FIG. 5(A).
Figure 5:
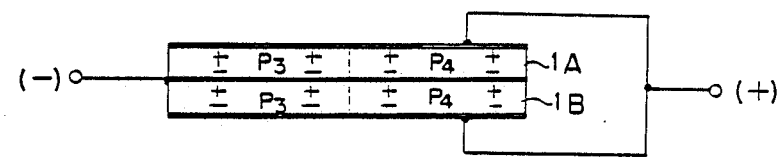
Figure 6:
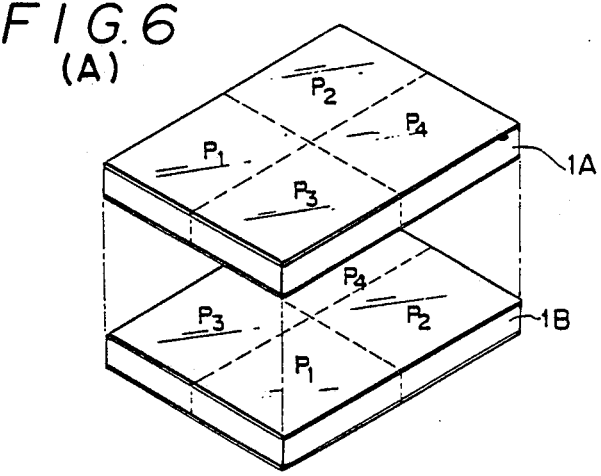
FIG. 6(A) is an exploded perspective view illustrating another example of the vibrator.
FIG. 6(B) is a side view illustrating the vibrator of FIG. 6(A).
Figure 6:
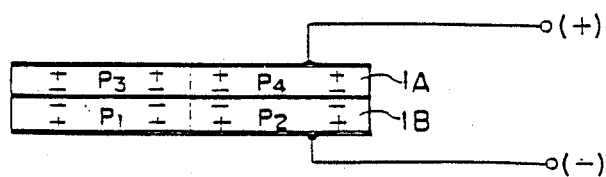
Figure 7:
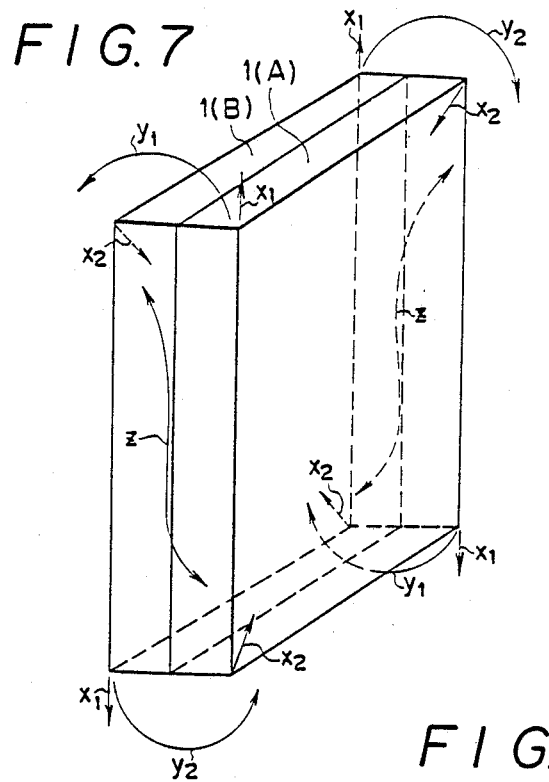
FIG. 7 is an explanatory perspective view illustrating twist vibration of the vibrator of FIG. 5(A) or FIG. 6(A).

The present invention will now be described with reference to the illustrated embodiment. FIG. 1 is a side view illustrating a detection structure of one embodiment of the specific gravity detector according to the present invention. The detection structure comprises an electromechanical vibrator 1, which will be described in detail later with reference to FIGS. 5 to 7, a transmission shaft 2 connected at one end thereof coaxially to one end of the vibrator 1, and a detector member 3 connected coaxially to the other end of the transmission shaft 2, whereby the detector member 3 can be vibrated about the common axis by the vibration of the vibrator 1 transmitted through the transmission shaft 2.

The transmission shaft 2 has the shape of a column or square pillar and serves not only as a carrier for supporting the detector member 3 at a location spaced from the vibrator 1 but also serves as a vibration transmission medium. The wavelength propagating along a resonance wave of the transmission shaft 2 when resonating is a function of the length of the transmission shaft 2. A mass 19 having a constant moment of inertial may be coaxially fitted about the transmission shaft 2 so that the resonant frequency of the vibrator 1 can be adjusted.

Figure 2:
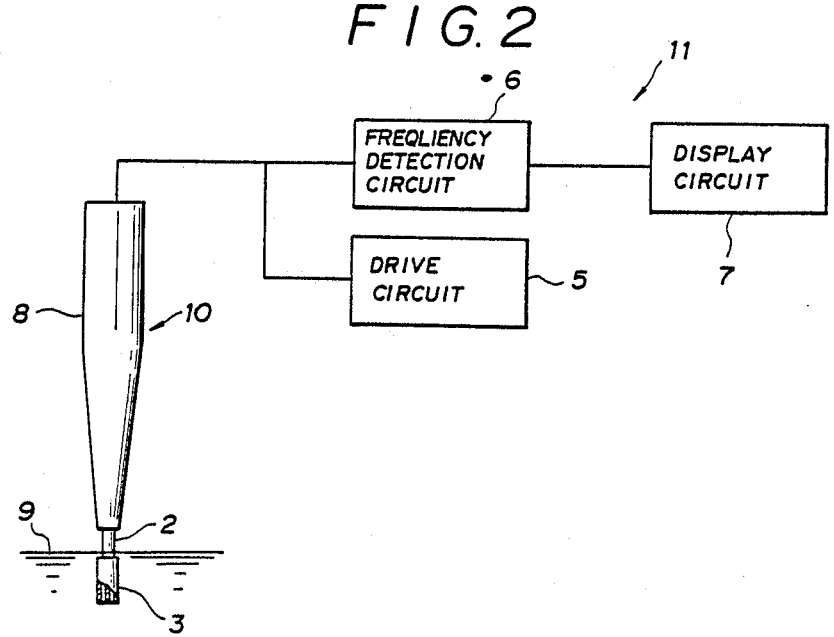
FIG. 2 is a schematic view illustrating the embodiment of FIG. 1 and detection circuit means connected thereto.
Figure 10:
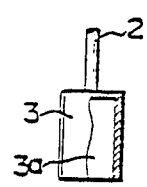
FIG. 10(A) is a partially cutaway side view illustrating one example of a detector member.
FIG. 10(B) is a cross-sectional view illustrating another example of the detector member.
Figure 10:
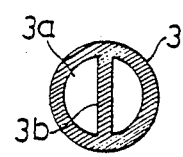

The detector member 3 is a hollow column having a circular cross section as illustrated in FIG. 10(A) and is made of metal or synthetic resin, and has a circumferential surface having a comparatively large surface area and subjected to mirror surface finishing. The hollow portion 3a of the detector member 3 is filled with liquid 9, the specific gravity of which is to be measured, when the detector member 3 is immersed in the liquid 9 and, in such a state, the detector member 3 is vibrated about its central axis by the vibrations transmitted through the transmission shaft 2 from the vibrator 1. The hollow portion 3a of the detector member 3 may be diametrically divided into two chambers by a partition wall 3b as illustrated in FIGS. 1, 2 or FIG. 10(B). At this time, the partition wall 3b serves as a resistance plate. The detector member 3 may be a solid column having a circular cross section, a thin plate, a cone or a spindle (not shown).

With the detection structure mentioned above, the vibration of the vibrator 1 about its central axis is transmitted through the transmission shaft 2 to the detector member 3 immersed in the liquid 9. Thus, the detector member 3 is vibrated within the liquid 9 about the common central axis of the vibrator 1, transmission shaft 2 and detector member. The vibration of the detector member 3 about the common axis within the liquid 9, is resisted due to the moment of inertia of the liquid 9 to increase the moment required to rotate the detector member 3. This increase in the moment varies the resonance frequency of the vibrator 1, and an electric signal corresponding to the variation in the resonance frequency is obtained from the vibrator 1. The detector member 3 vibrating about the common central axis does not generate a wave which would be a disturbance factor as does a vibrator vibrating in the direction of its thickness, thereby maintaining the liquid 9 in a static state and being only subjected to the inertial resistance.

As illustrated in FIG. 2, a measuring device 11 has detection circuit means which comprises a drive circuit 5 for electrically driving the vibrator 1, a frequency detection circuit 6 for detecting, as an electric signal, the variation in the resonance frequency of the vibrator 1, and a display circuit 7 operable in response to the variation in the resonance frequency to display the specific gravity, and which is connected to the vibrator 1.

As illustrated in FIG. 3, part of the transmission shaft 2 and the entire detector member 3 are exposed, whereas the remaining part of the transmission shaft 2 and the entire vibrator 1 are incorporated into a handgrip type housing 8. The exposed detector member 3 is immersed in the liquid 9 as illustrated in FIG. 2. A detection section 10 is connected via a connector cable 12 to the measuring device 11 comprising the detection circuit means as illustrated in FIG. 3.

The electromechanical vibrator 1 vibrating about its central axis will now be described. FIGS. 5(A) and 5(B) illustrate one example of the vibrator which comprises a pair of piezoelectric ceramic members 1A and 1B having a rectangular shape and attached to each other. Each of the piezoelectric ceramic members 1A and 1B is divided into four quadrants $P_1$, $P_2$, $P_3$ and $P_4$. The two diagonal quadrants $P_1$ and $P_4$ constitute negative-direction polarization sections and the two remaining diagonal quadrants $P_2$ and $P_3$ constitute positive-direction polarization sections. Furthermore, the upper and lower surfaces of each of the piezoelectric ceramic members 1A and 1B are coated with electrodes V. The two piezoelectric ceramic members 1A and 1B are attached to each other so that the lengthwise vibration of the positive-direction polarization sections $P_2$ and $P_3$ is opposite to that of the negative-direction polarization sections $P_1$ and $P_4$ when voltage is applied to the two piezoelectric ceramic members 1A and 1B. To be specific, in a parallel circuit, the two piezoelectric ceramic members 1A and 1B are attached to each other, as illustrated in FIG. 5(B), so that the sections $P_1$, $P_2$, $P_3$ and $P_4$ of one member respective face the sections $P_1$, $P_2$, $P_3$ and $P_4$ of the other member.

FIGS. 6(A) and 6(B) illustrate another example of the vibrator 1, wherein two piezoelectric ceramic members 1A and 1B each having the upper and lower surfaces thereof coated with electrodes V are attached to each other so that the sections $P_1$, $P_2$, $P_3$ and $P_4$ of one member face the sections $P_3$, $P_4$, $P_1$ and $P_2$ of the other member, respectively. This arrangement of the positive-direction and negative-direction polarization sections can advantageously be used in a series circuit as illustrated in FIG. 6(B).

With the arrangement illustrated in FIGS. 5(B) or 6(B), one of a pair of facing sections elongates and the other contracts to allow the pair of facing sections to be bent to one side of the vibrator with respect to the thickness direction of whereas one of an adjacent pair of facing sections contracts and the other elongates to allow the adjacent pair of facing sections to be bent to the other side of the vibrator with respect to direction of thickness. Thus, twist vibration is induced. This will be described more specifically below with reference to FIG. 7.

With regard to the positive-direction polarization sections $P_2$ and $P_3$, the piezoelectric ceramic member 1A elongates in the direction of $x_1$, whereas the piezoelectric ceramic member 1B contracts in the direction of $x_2$. In this case, therefore, the positive-direction polarization sections $P_2$ and $P_3$ are bent to one side with respect to the thickness direction, i.e. in the direction of $y_1$. With regard to the negative-direction polarization sections $P_1$ and $P_4$, the piezoelectric ceramic member 1A contracts in the direction of $x_2$, whereas the piezoelectric ceramic member 1B elongates in the direction of $x_1$. In this case, therefore, the negative-direction polarization sections $P_1$ and $P_4$ are bent to the other side with respect to the thickness direction, i.e. in the direction of $y_2$. In this way, the vibrator 1 vibrates in the clockwise direction at one end thereof and in the counterclockwise direction at the other end thereof the produce twist vibration about the central axis thereof.

The vibrator 1 having one end thereof connected to the transmission shaft 2 has the other end thereof fixed integrally to an inertia mass 13 as illustrated in FIG. 1 or FIG. 4(A). The inertia mass 13 is incorporated into the housing 8 and is fixed therein by vibration absorbing members 14 tightly fitted on the inner wall of the housing 8 under friction and supported on a receiving portion 15 formed inside the housing 8. Thus, the inertia mass is prevented from moving and is maintained in position as illustrated in FIG. 4(A). The vibrator 1 is vibrated at a resonance frequency so that a node 17 of a resonance wave having a waveform 16 is located on the transmission shaft 2, e.g. on the leading end of the housing 8 which is sealed with a sealing member 18, as illustrated in FIG. 4(B). The sealing member 18 supports the transmission shaft 2 and prevents the liquid 9 from entering the housing 8.

Since one end of the vibrator 1 is fixed to the inertia mass 13, as described above, the other end of the vibrator 1 vibrates about its central axis and the vibration thereof is transmitted to the detector member 3 through the transmission shaft 2, thereby vibrating the detector member 3 about the transmission shaft 2 to detect the specific gravity of the liquid 9 in the form of an equivalent electric signal from the variation in resonance frequency.

Figure 8:
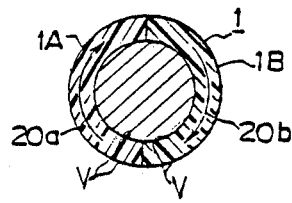
FIG. 8 is a cross-sectional view illustrating still another example of the vibrator.
Figure 9:
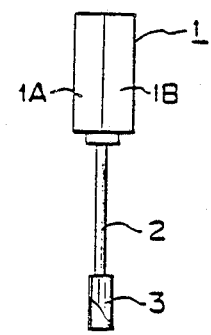
FIG. 9 is a side view illustrating the detection structure having the vibrator of FIG. 8.

FIGS. 8 and 9 illustrate still another example of the vibrator 1. In this example, the vibrator 1 is formed of piezoelectric ceramic material the shape of a hollow cylinder divided vertically into two equal segments 1A and 1B having inner and outer circumferential surfaces subjected to polarization treatment (poling) so that the polarization directions 20a and 20b are opposite, and coated with electrodes V. One end of the transmission shaft 2 is fitted into the hollow portion of the hollow cylindrical vibrator 1 while the outer circumferential surfaces of the vibrator 1 is held in a fixed state. Conversely, one end of the transmission shaft 2 may be fitted about the hollow cylindrical vibrator 1 while the inner circumferential surface of the vibrator 1 is held in a fixed state (not shown). In this state, the vibrator 1 is electrically driven at the inner or outer circumferential surface thereof with the center thereof being a vibrating axis. Therefore, the vibration of the vibrator 1 is transmitted to the detector member 3 through the transmission shaft 2 in the same manner as described above, thereby detecting the specific gravity of the liquid 9 from the variation in the resonance frequency of the vibrator corresponding to the moment of inertia of the liquid.

As has been described in the foregoing description, according to the present invention, since a detector member is vibrated about its central axis with an electromechanical vibrator used as a vibration source to thereby detect the specific gravity of liquid, the generation of a wave within the liquid, which would be a disturbance factor that is known to be produced when using a commercially available vibrator vibrating in its direction of thickness, can be effectively prevented to thereby make it possible to measure the specific gravity of the liquid over a wide range with a high degree of precision.

Furthermore, the specific gravity detector according to the present invention can be compact and light as compared with the conventional float-type or tuning fork-type specific gravity detector, and is not limited with respect to operating conditions.

In addition, according to the present invention, the vibration of the detector member can be obtained with ease, and the detection structure can simply be provided inexpensively.

What is claimed is:

1. A specific gravity detector for detecting the specific gravity of a liquid, said detector comprising:
    an inertia mass fixed in the detector;
    an electromechanical vibrator rigidly connected to said inertial mass and having a central axis, said vibrator capable of vibrating about the central axis;
    a transmission shaft connected to said vibrator at one end thereof and extending coaxially therefrom;
    a detector member connected to said transmission shaft at the other end thereof and extending coaxially therefrom, said detector member vibratable via said transmission shaft by said vibrator about the central axis thereof; and
    resonant frequency establishing means for establishing a desired resonant frequency of said vibrator, said resonant frequency vibration means comprising a mass having a predetermined moment of inertial and fitted around said transmission shaft at a locating thereon spaced from said vibrator by a distance corresponding to said desired resonant frequency.

2. A specific gravity detector for detecting the specific gravity of a liquid as claimed in claim 1, wherein said detector member has a hollow portion.

* * * * *